United States Patent [19]

Iwamoto et al.

[11] Patent Number: 5,092,888
[45] Date of Patent: Mar. 3, 1992

[54] HARDENING MATERIAL

[75] Inventors: Osamu Iwamoto; Yasuhiro Ogawa, both of Tsukuba, Japan

[73] Assignee: Tokuyama Soda Kabushiki Kaisha, Tokuyama, Japan

[21] Appl. No.: 524,480

[22] Filed: May 17, 1990

[30] Foreign Application Priority Data

May 19, 1989 [JP] Japan .................................. 1-124236

[51] Int. Cl.$^5$ .............................................. A61F 2/28
[52] U.S. Cl. ..................................................... 623/16
[58] Field of Search .................... 623/1, 11, 12, 16, 18, 623/66; 433/199, 201, 202

[56] References Cited

U.S. PATENT DOCUMENTS

| | | | |
|---|---|---|---|
| 4,440,750 | 4/1984 | Glowacki et al. | 623/16 |
| 4,518,430 | 5/1985 | Brown et al. | 433/199 |
| 4,808,184 | 2/1989 | Tepic | 623/16 |
| 4,917,702 | 4/1990 | Scheicher et al. | 623/16 |

*Primary Examiner*—David J. Isabella
*Attorney, Agent, or Firm*—Sherman and Shalloway

[57] ABSTRACT

Disclosed is a hardening material comprising (a) a powder component composed of a powdery mixture of tetracalcium phosphate and calcium phosphate having a Ca/P atomic ratio lower than 1.67 and (b) a liquid component composed of a colloidal aqueous solution comprising solid colloid particles dispersed in an aqueous medium, wherein said components (a) and (b) are independently packed and both the components are mixed for hardening.

This hardening material can give a hardened body having a high strength without showing any harmful action on a living body. Accordingly, this hardening material is especially effectively used for the restoration of a hard tissue of a living body.

15 Claims, No Drawings

HARDENING MATERIAL

BACKGROUND OF THE INVENTION

(1) Field of the Invention

The present invention relates to a novel hardening material. More particularly, the present invention relates to a hardening material having excellent performances as a bone-restoring hardening material. More specifically, the present invention provides a hardening material comprising (a) a powder component composed of a powdery mixture of tetracalcium phosphate and calcium phosphate having a Ca/P atomic ratio lower than 1.67 and (b) a liquid component composed of a colloidal aqueous solution comprising solid colloid particles dispersed in an aqueous medium, wherein said components (a) and (b) are independently packed and both the components are mixed for hardening.

(2) Description of the Related Art

Various hardening materials have been developed and practically used. However, few of them are satisfactorily used in the fields where a high strength is required, for example, for restoring hard tissues of a living body, e.g., setting a broken bone or filling a tooth defect. At the present, development of a hardening material capable of exhibiting a high strength is especially desired in the field of therapeutic materials, for example, medical materials such as a filling material for a bone defect and a luting filling material for an artificial bone or artificial articulation, and dental materials such as a luting cement, a filling cement, a temporary sealing cement, a root canal filling material and a cavity lining material. Materials used in this field are required to have a good affinity with a tooth or bone and a much reduced harmful effect and show a high strength.

As the hardening material to be used in this field, there have been proposed materials forming hydroxyapatite which is a main component of teeth or bone. For example, a hardening material comprising tetra calcium phosphate, calcium hydrogenphosphate anhydride or dihydrate and water forms hydroxyapatite and hardens when mixed (see U.S. Pat. No. 4,518,430 and U.S. Pat. No. 4,612,053).

In the hardened body obtained from this hardening material, in general, the strength is not sufficiently improved, and this hardening material is defective in that the hardening material cannot be applied to a part for which a high strength is required. As the material for improving the strength, there has been proposed a hardening material comprising powdery tetracalcium phosphate as the powder component and an aqueous solution of an organic acid such as citric acid, succinic acid or malic acid as the liquid component (see Japaneses Unexamined Patent Publication No. 62-72363). However, this hardening material is defective in that since a calcium salt of the organic acid is formed as a by-product and the obtained hardened body comes to have a high water solubility, when the material is used as a dental filling material, the hardened body is dissolved during a long period of time.

Furthermore, use of an aqueous solution of a polymer of an unsaturated carboxylic acid as the liquid component has been proposed (Japanese Unexamined Patent Publication No. 62-72363). However, according to this proposal, a harmful effect of causing inflamation in a living body tissue by the unreacted carboxylic acid is brought about at the initial stage of mixing, and the proposed hardening material is not completely satisfactory.

SUMMARY OF THE INVENTION

We indertook research with a view to overcoming the foregoing defects of the conventional techniques, and as a result, it was found that if a powder component comprising tetracalium phosphate and specific calcium phosphate is mixed with a specific colloidal aqueous, solution, a hardened body having a high strength can be obtained without any harmful effect on a living body. We have now completed the present invention.

More specifically, in accordance with the present invention, there is provided a novel hardening material comprising (a) a powder component composed of a powdery mixture of tetracalcium phosphate and calcium phosphate having a Ca/P atomic ratio lower than 1.67 and (b) a liquid component composed of colloidal aqueous solution comprising solid colloid particles dispersed in an aqueous medium, wherein said components (a) and (b) are independently packed and both the components are mixed for hardening.

DETAILED DESCRIPTION OF THE INVENTION

One ingredient of the powder component (b) constituting the hardening material of the present invention is tetracalcium phosphate, which is a known compound represented by the formula of $Ca_4P_2O_9$. The process for preparing tetracalcium phosphate used in the present invention is not particularly critical. The preparation process generally adopted is described below.

Calcium compounds such as $CaCO_3$, $CaO$ and $Ca(OH)_2$ are generally used as the calcium source, and phosphorus compounds such as $P_2O_5$, $H_3PO_4$, $NH_4H_2PO_4$ and $(NH_4)_2HPO_4$ are used as the phosphorus source, and alternatively compounds containing both of Ca and P, such as $CaHPO_4 \cdot 2H_2O$, $CaHPO_4$, $Ca(H_2O_4)_2$ and $Ca_2P_2O_7$ are preferably used as the starting material. The procedures for preparing tetracalcium phosphate differ according to combination of the starting compounds. For example, a dry method comprising mixing $\gamma\text{-}Ca_2P_2O_7$ obtained by calcining $CaHPO_4 \cdot 2H_2O$ with $CaCO_3$ and calcining the mixture is preferably adopted. This reaction is expressed by the following reaction formula, and if the obtained $Ca_4P_2O_9$ is calcined at a temperature higher than 1200° C. and rapidly cooled outside the furnace, or if the obtained $Ca_4P_2O_9$ is calcined at a temperature higher than 1200° C. and cooled in a nitrogen atmosphere, pure tetracalcium phosphate can be obtained without conversion to hydroxyapatite [$Ca_{10}(PO_4)_6(OH)_2$]:

$$2CaHPO_4 \cdot 2H_2O \rightarrow \gamma\text{-}Ca_2P_2O_7 + 3H_2O$$

$$Ca_2P_2O_7 + 2CaCO_3 \rightarrow Ca_4P_2O_9 + 2CO_2$$

Another ingredient of the powder component (a) constituting the hardening material of the present invention is calcium phosphate having a Ca/P atomic ratio lower than 1.67. This Ca/P atomic ratio is a requirement necessary for forming hydroxyapatite efficiently. As the calcium phosphate having a Ca/P atomic ratio of 1.67 or higher in the pure form, there are present hydroxyapatite and tetracalcium phosphate, but if they are used, it is impossible to form hydroxyapatite efficiently at the hardening step, and the intended hardening material providing a hardened body having a high strength cannot be obtained.

Known calcium phosphate can be used without any particular limitation, if the Ca/P atomic ratio is lower than 1.67. For example, $Ca(H_2PO_4)_2 \cdot 2H_2O$, $CaHPO_4 \cdot 2H_2O$, $CaHPO_4$, $Ca_8H_2(PO_4)_6 \cdot 5H_2O$, $Ca_3(PO_4)_2$ and $Ca_2P_2O_7$ are preferably used, and $CaHPO_4 \cdot 2H_2O$ and $CaHPO_4$ are especially preferably used because the reaction velocity is high and the mechanical properties of the hardened body are most highly improved.

The above-mentioned two ingredients of the powder component form hydroxyapatite, for example, by the following reaction when $CaHPO_4 \cdot 2O$ is used as the calcium phosphate:

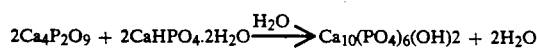

$$2Ca_4P_2O_9 + 2CaHPO_4 \cdot 2H_2O \xrightarrow{H_2O} Ca_{10}(PO_4)_6(OH)_2 + 2H_2O$$

In the powder component of the hardening material of the present invention, the mixing ratio between tetracalcium phosphate and calcium phosphate having a Ca/P atomic ratio lower than 1.67 differs according to the kind of the calcium phosphate and is not simply defined. However, the mixing ratio between the two ingredients is preferably selected so that the Ca/P atomic ratio in the whole powder component (a) is in the range of from 1.3 to 1.8.

The tetracalcium phosphate and calcium phosphate are used in the form of a powder mixture, but the particle sizes of the this powder mixture are not particularly critical. In general, however, the average particle size of the tetracalcium phosphate is from 0.1 to 100 $\mu m$, preferably from 0.5 to 50 $\mu m$, and the average particle size of the calcium phosphate having a Ca/P atomic ratio lower than 1.67 is from 0.1 to 50 $\mu m$, preferably from 0.1 to 10 $\mu m$.

The liquid component (b) of the hardening material of the present invention is a colloidal aqueous solution comprising solid colloid particles dispersed in an aqueous medium. Various colloidal aqueous solutions of this type are known, and in general, these aqueous solutions are divided into "sols" comprising inorganic solid particles dispersed in an aqueous medium and "latexes" comprising organic polymer particles dispersed in an aqueous medium. In the present invention, any of known sols and latexes can be used without any particular limitation. A sol comprising inorganic oxide particles, such as a silica sol or alumina sol, or a so-called polymer latex such as a latex of polymethyl methacrylate or polystyrene, is preferably used as the liquid component (b) in the present invention. In view of the crystallinity, the affinity with a living body and the increase of the compressive strength in the hydroxyapatite formed by the mixing of the components (a) and (b), a sol comprising inorganic oxide particles is preferably used, and in the field where the safety to a living body and the storage stability are important, a silica sol or alumina sol is especially preferably used.

The concentration of the solid colloid particles in the colloidal aqueous solution used in the present invention differs according to the kind of the colloid particles. However, in general, if this concentration is too low, the intended object of the present invention cannot be attained. In contrast, if the concentration is too high, the compatibility with the powder component is degraded or the improvement of the strength in the obtained hardened body is insufficient. Accordingly, it is preferred that the concentration is from 5 to 60% by weight, especially from 10 to 50 % by weight.

The components (a) and (b) of the present invention are independently packed, and both the components are mixed at the hardening step to form a hardened body. The mixing ratio between the powder component and liquid component is appropriately selected so that a viscosity suitable for the intended use is attained and the strength is sufficiently improved. In general, it is preferred that the powder/liquid mixing weight ratio (P.L ratio) be in the range of from 0.5 to 5, especially from 2 to 4.

Other ingredients can be added to the hardening material of the present invention according to need, so far as bad influences are not imposed on the hardening property. For example, in order to impart an X-ray radio-opaque property, barium sulfate, barium glass, strontium glass, zirconia or iodoform is preferably added in an amount of 10 to 50 parts by weight per 100 parts by weight of the hardening material. Moreover, hydroxyapatite, silica, calcium fluoride, titanidum dioxide, calcium hydroxide, alumina, sodium phosphate or ammonium phosphate can be added so as to adjust the setting time and the strength.

The reason why the hardening material of the present invention provides a hardened body having a high strength has not been completely elucidated. However, it is presumed that in addition to the effect of reducing the water content in the hardened body, the colloid particles having a size of 1 nm to 1 $\mu m$ will exert a certain function on the formation of crystal nuclei of hydroxyapatite and will have a favorable influence on the growth of crystals of hydroxyapatite, with the result that an unexpectedly high increase of the mechanical strength will the attained.

The hardening material of the present invention can be formed into a hardened body having a high strength without any harmful action on a living body. Accordingly, the hardening material can be valuably used for the restoration of hard tissues of a living body. Especially, the hardening material of the present invention is preferably used as a restorative material such as a cavity lining material, a luting cement, a filling cement or a plastic restoration bone cement.

The present invention will now be described in detail with reference to the following examples that by no means limit the scope of the invention. The definitions and measurement methods of the factors mentioned in the text and examples of the specification are described below.

(1) Average Particle Size of Powder

A sample powder was dispersed in isopropyl and the average particle size was measured by a particle size distribution meter (CAPA-500 supplied by Horiba Seisakusho) according to the centrifugal sedimentation method.

(2) Structure

The X-ray diffraction pattern of a sample powder was determined by using an X-ray diffractometric apparatus (supplied by Nippon Denshi) to identify the structure of calcium phosphate.

(3) Consistency

A mixed mixture (1 g) formed by mixing a powder component with a liquid component was placed in a substantially circular mold having a diameter of up to 10 mm on a glass sheet having a size of 100 mm × 100 mm, and when three minutes had passed from the start of the mixing, a glass sheet having a mass of 120 g was placed on the mixed mixture. When ten minutes had passed from the start of the mixing, the lengths of largest and smallest portions of the circle formed by the mixed mixture were measured and the mean value was calculated as the consistency.

(4) Setting Time of Mixed Mixture

A mixed mixture obtained by mixing powder and liquid components for 1 minute was filled in a polyvinyl chloride mold having an inner diameter of 20 mm and a thickness of 3 mm and the surface of the filled mixed mixture was flattened. When 2 minutes and 30 seconds had passed from the start of the mixing, the mixed mixture was transferred into a constant temperature bath maintained at a temperature of 37° C. and a relative humidity of 100%. Then, a Gillmore needle having a weight of 114.12 g (the sectional area of the needle was 4.91 mm$^2$) was quietly dropped on the surface of the test piece. The time when it became impossible to discern the needle mark was counted from the point of the start of the mixing and designated as the setting time.

(5) Compressive Strength

A sample was subjected to the crushing strength test for zinc phosphate cement according to JIS T-6602.

More specifically, a powder component and a liquid component were mixed for 1 minute, and the mixed mixture was charged in a mold (having a diameter of 6 mm and a depth of 12 mm) and the mold was placed in a constant temperature bath maintained at a temperature of 37° C. and a relative humidity of 100% for 24 hours. By using a universal Tensilon tester (supplied by Toyo-Boldwin), the test piece was pressed at a crosshead speed of 0.5 mm/min until the test piece was crushed. The crushing strength was measured as the compressive strength (kg/cm$^2$).

EXAMPLE 1

$\gamma$-Ca$_2$P$_2$O$_7$ was obtained by calcining CaHPO$_4$·2H$_2$O at 500° C. for 2 hours. The obtained powder was mixed with powdery CaCO$_3$ at a molar ratio of ⅔ and the mixture was calcined at 1400° C. for 2 hours in air and rapidly cooled outside the furnace. From the X-ray diffraction diagram of the product, it was confirmed that the formed powder was tetracalcium phosphate. This tetracalcium phosphate was pulverized for 10 hours by an alumina ball mill. The pulverized product was passed through a 250-mesh sieve to obtain pulverized tetracalcium phosphate (having an average particle size of 5.29 μm and a bulk density of 1.20 g/cm$^3$).

The obtained tetracalcium phosphate was mixed with calcium hydrogenphosphate anhydride (having an average particle size of 1.2 μm) so that the Ca/P atomic ratio was 1.67.

The obtained mixed powder as the powder component was mixed with a coloidal silica having a silica concentration of 40% by weight and a particle size of 16 to 20 μm (Cataloid S140 supplied by Shokubai Kasei Kogyo) at a powder/liquid ratio of 3.0. The consistency of the mixed mixture was 28 mm, the setting time was 16 minutes 30 seconds, and the compressive strength was 710 kg/cm$^2$. By X-ray diffractometry, it was confirmed that the hardened body was composed of hydroxyapatite.

EXAMPLE 2 AND COMPARATIVE EXAMPLE 1

The procedure of Example 1 were repeated in the same manner except that the powder component used in Example 1 was mixed with a colloidal silica having a concentration shown in Table 1. The consistency and compressive strength were measured. The obtained results are shown in Table 1. In Comparative Example 1, the powder component was mixed with water instead of the colloidal silica. The consistency and compressive strength were measured. The obtained results are shown in Table 1.

TABLE 1

| | Concentration (% by weight) of Colloidal Silica | Consistency (mm) | Setting Time | Compressive Strength (kg/cm$^2$) |
| --- | --- | --- | --- | --- |
| Run 1 of Example 2 | 20 | 29 | 17 minutes and 30 seconds | 470 |
| Run 2 of Example 2 | 30 | 28 | 17 minutes and 30 seconds | 520 |
| Run 3 of Example 2 | 50 | 27 | 16 minutes | 705 |
| Run 4 of Example 2 | 55 | 24 | 15 minutes and 30 seconds | 620 |
| Comparative Example 1 | water | 28 | 19 minutes | 180 |

EXAMPLE 3

The tetracalcium phosphate obtained in Example 1 was mixed with calcium hydrogenphoshate dihydrate so that the Ca/P atomic ratio was 1.55, and the mixture was pulverized by a vibration mill for 10 minutes. The obtained mixture as the powder component was mixed with the same colloidal silica as used in Example 1 at a powder/liquid ratio of 2.8. It was found that the consistency was 29 mm, the setting time was 13 minutes and the compressive strength was 930 kg/cm$^2$.

EXAMPLE 4

A hardened body was prepared in the same manner as described in Example 3 except that an alumina sol having an alumina concentration of 10% by weight and comprising aluminum fibers having a length of 100 mu and a diameter of 10 mμ (AS-2 supplied by Shokubai Kasei Kogyo) was used instead of the colloidal silica. It was found that the consistency was 28 mm, the setting time was 14 minutes and the compressive strength was 580 kg/cm$^2$.

EXAMPLE 5 AND COMPARATIVE EXAMPLE 2

The tetracalcium phosphate powder obtained in Example 1 was mixed with powder tricalcium $\gamma$-phosphate (having an average particle size of 2.5 μm) so that the Ca/P atomic ratio was 1.6. The obtained powder mixture was mixed with the same colloidal silica as used in Example 1 at a powder/liquid ratio of 2.5. It was found that the consistency was 28 mm, the setting time was 2 hours and 30 minutes and the compressive strength was 490 kg/cm$^2$.

For comparison, the above-mentioned powder mixture was mixed with water instead of the colloidal silica. It was found the consistency was 28 mm, the setting time was 3 hours and 40 minutes and the compressive strength was 180 kg/cm$^2$.

EXAMPLE 6

The procedures of Example 1 were repeated in the same manner except that a polystyrene latex having a polystyrene concentration of 7% by weight and a polystyrene particle size of 0.2 μm were used instead of the colloidal silica. It was found that the consistency was 27 mm, the setting time was 18 minutes and the compressive strength was 290 kg/cm$^2$.

We claim:

1. A hardening material comprising (a) a powder component composed of a powdery mixture of tetracalcium phosphate and calcium phosphate having a Ca/P atomic ratio lower than 1.67 and (b) a liquid component composed of a colloidal aqueous solution comprising solid colloid particles dispersed in an aqueous medium, wherein said components (a) and (b) are independently packed and both the components are mixed for hardening.

2. A hardening material as set forth in claim 1, wherein the average particle size of the tetracalcium phosphate is from 0.1 to 100 μm and the average particle size of the calcium phosphate having a Ca/P atomic ratio lower than 1.67 is from 0.1 to 50 μm.

3. A hardening material as set forth in claim 1, wherein the average particle size of the colloid particles is from 1 nm to 1 μm.

4. A hardening material as set forth in claim 1, wherein the concentration of the solid colloid particles in the colloidal aqueous solution is from 5 to 60% by weight.

5. A hardening material as set forth in claim 1, wherein the colloidal aqueous solution is selected from the group consisting of a silica sol, alumina sol and a polymer latex.

6. An implantable hardening material for the restoration of a hard tissue of a living body, which comprises (a) a powder component composed of a powdery mixture of tetracalcium phosphate and calcium phosphate having a Ca/P atomic ratio lower than 1.67 and (b) a liquid component composed of a colloidal aqueous solution comprising solid colloid particles dispersed in an aqueous medium, wherein said components (a) and (b) are independently packed and both the components are mixed for hardening.

7. The hardening material as set forth in claim 1, wherein the calcium phosphate is selected from CaHPO$_4$·2H$_2$O and CaHPO$_4$.

8. The hardening material of claim 1, wherein the Ca/P atomic ratio of tetracalcium phosphate and calcium phosphate is in the range of from 1.3 to 1.8.

9. The hardening material as set forth in claim 1, wherein the average particle size of the tetracalcium phosphate is from 0.5 to 50 μm and the average particle size of the calcium phosphate is from 0.1 to 10 μm.

10. The hardening material as set forth in claim 1, wherein the aqueous solution is selected from alumina sol and silica sol.

11. The hardening material as set forth in claim 1, wherein the concentration of the solid colloidal particles in the colloidal aqueous solution is from 10 to 50% by weight.

12. The hardening materials as set forth in claim 6, wherein compounds (a) and (b) are combined in a mixing ratio of from 0.5 to 5.

13. The hardening material as set forth in claim 6, wherein the mixing ratio of components (a) and (b) is from 2 to 4.

14. The hardening material of claim 1, further comprising a constituent selected from barium sulfate, barium glass, strontium glass, zirconia and iodoform.

15. The hardening material of claim 14, wherein the constituent is added in an amount of 10 to 50 parts by weight per 100 parts by weight of the hardening material.

* * * * *